United States Patent Office

Re. 24,763
Reissued Jan. 12, 1960

24,763

POLYTHIONATE COMPOUND AT MOST SOMEWHAT SOLUBLE IN WATER

Torben Emil Neesby, Boonton, N.J., assignor to Carroll Dunham Smith Pharmacal Co., a corporation of New Jersey No Drawing. Original No. 2,815,344, dated December 3, 1957, Serial No. 509,695, May 19, 1955. Application for reissue June 3, 1959, Serial No. 817,962

9 Claims. (Cl. 260—247.1)

Matter enclosed in heavy brackets [ ] appears in the original patent but forms no part of this reissue specification; matter printed in italics indicates the additions made by reissue.

This invention relates to novel polythionates and to their preparation.

This application is a continuation-in-part of my copending application Serial No. 315,827 filed October 20, 1952, and now abandoned.

Inorganic salts of polythionates, including stabilized aqueous solutions thereof, have found application in the cosmetic and other fields as adjuvants for different products, such as hair tonics, etc. Where, however, it is desired to apply such polythionates to cosmetics containing alcohol or consisting chiefly of fatty or waxy materials, difficulties have been encountered because of their poor solubility in such media. Another objection to alkali metal polythionates heretofore used is that in order to maintain them stabilized it is generally necessary to maintain them at a low pH, e.g., 3 or less. This seriously interferes with their use in many fields in which neutral or slightly acid conditions are desired.

It is among the objects of this invention to provide a stable polythionate composition which is soluble in alcohol and remains stable in acid or neutral media.

Another object is to provide a polythionate composition which in addition to the therapeutic properties attributable to the presence of the polythionate radical, has desirable germicidal properties.

Still another object of the invention is to provide a method of producing such polythionate compositions.

Other objects and advantages of this invention will be apparent from the following detailed description thereof.

The novel polythionate compounds are of the general structural formula:

$$Q_2S_xO_6$$

in which Q is:

(1) A quaternary ammonium radical, having four alkyl groups, $R_1$ $R_2$, $R_3$ and $R_4$, of which $R_1$ preferably contains from 8 to 20 carbon atoms, and each of the others contains from 1 to 3 carbon atoms; or (2) Dialkyl morpholinium or dialkyl piperidinium, wherein one of the alkyl groups contains from 8 to 20 carbon atoms and the other from 1 to 3 carbon atoms; or (3) Alkyl pyridinium or alkyl iso-quinolinium, wherein the alkyl group contains from 8 to 20 carbon atoms; or (4) Tri-alkyl phenyl alkyl *ammonium* in which the phenyl alkyl group contains from 7 to 15 carbon atoms, one of the other alkyl groups containing 8 to 20 carbon atoms and the other 1 to 3 carbon atoms; or (5) Alkyl phenyl alkyl morpholinium or piperidinium in which the alkyl group contains 8 to 20 carbon atoms and the phenyl alkyl group 7 to 15 carbon atoms;

x has a value of from 3 to 10, inclusive, preferably 3 to 6, inclusive; and the cation, such as the quarternary ammonium base portion of the compound has a molecular weight of from 190 to 470 and the polythionate anion has a molecular weight of from 192 to 288 or higher up to about 416.

The formula for the quaternary ammonium polythionate is as follows:

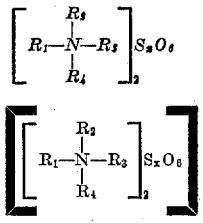

(1)

in which $R_1$ is an alkyl group containing from 8 to 20 carbon atoms and each of $R_2$, $R_3$, and $R_4$ is an alkyl group containing from 1 to 3 carbon atoms.

The formula for the morpholinium polythionate is as follows:

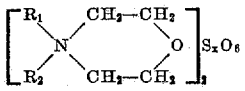

(2)

in which $R_1$, $R_2$ and x have the values above noted.

The formula for the piperidinium compound of this invention is as follows:

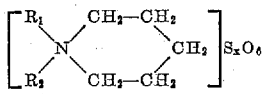

(3)

in which $R_1$ and $R_2$ and x have the values above noted.

The formula for the pyridinium compound is as follows:

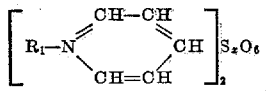

(4)

in which $R_1$ and x have the values above noted.

The formula for the iso-quinolinium compound is as follows:

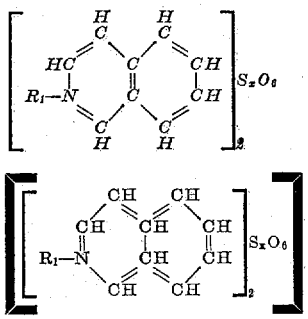

(5)

in which $R_1$ and x have the values above noted.

Examples of such compounds are:

(1) Bis-(lauryl trimethyl ammonium) trithionate, tetrathionate, pentathionate, hexathionate, and other higher polythionates.

(2) Bis-(lauryl dimethyl benzyl ammonium) trithionate, tetrathionate, pentathionate, hexathionate, and higher polythionates.

(3) Bis-(octa decyl trimethyl ammonium) trithionate, tetrathionate, pentathionate, hexathionate, and higher polythionates.

(4) Bis-(N-lauryl pyridinium) trithionate, tetrathionate, pentathionate, hexathionate, and higher polythionates.

(5) Bis-(cetyl dimethyl benzyl ammonium) trithionate, tetrathionate, penthathionate, hexathionate, and higher polythionates.

(6) Bis-(octadecyl trimethyl ammonium) trithionate, tetrathionate, penthathionate, hexathionate, and higher polythionates.

(7) Bis-(hexadecyl trimethyl ammonium) trithionate, tetrathionate, penthathionate, hexathionate, and higher polythionates.

(8) Bis-(dodecyl acetamido dimethyl benzyl ammonium) trithionate, tetrathionate, pentathionate, hexathionate, and higher polythionates.

(9) Bis-(para-alkyl tolyl methyl trimethyl ammonium) trithionate, tetrathionate, pentathionate, hexathionate, and higher polythionates.

(10) Bis-(para-di-isobutyl phenoxy ethoxy ethyl dimethyl benzyl ammonium) trithionate, tetrathionate, penthathionate, hexathionate, and higher polythionates.

(11) Bis-(N-lauryl N-methyl morpholinium) trithionate, tetrathionate, pentathionate, hexathionate, and higher polythionates.

(12) Bis-(N-lauryl N-methyl piperidinium) trithionate, tetrathionate, pentathionate, hexathionate, and higher polythionates.

(13)

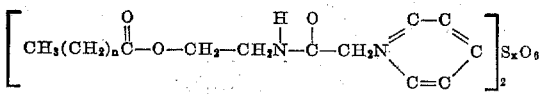

in which n equals 8 to 16 and x has a value of from 3 to 10; when n is 10 the compound is bis-(N-(lauroyl colamino formyl-methyl) pyridinium) polythionate.

(14)

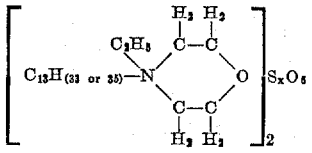

Bis-(N-fatty radical (from soya oil containing 33 or 35 hydrogen atoms)-N-ethyl morpholinium) polythionate.

In compound 9 above the alkyl group contains 12 carbon atoms.

The novel crude quaternary ammonium polythionates are wax-like compounds. Upon purification, for example, by filtration with activated carbon and crystallization from solution, they are semi-crystalline or crystalline in character. Compounds of penta, hexa and higher polythionates are substantially insoluble in water provided that the cation (quaternary ammonium base) has a molecular weight of 232 or more. Tetrathionate compounds having a molecular weight below 232 are somewhat soluble in water. These compounds generally form viscous aqueous solutions.

The substantial insolubility in water of the penta, hexa and higher polythionates is indeed surprising because both the quaternary ammonium base and the polythionates are readily soluble in water, and the polythionic acids are known to be very strong acids, even stronger than sulfuric acid. Unexpectedly, however, I have found that the reaction of a quaternary ammonium base having a molecular weight in excess of 232 and of the type hereinabove set forth, and a penta or higher polythionate results in quaternary ammonium polythionate compounds which are practically insoluble in water. They are stable, i.e. do not readily decompose, and this is the case even when the media in which they are incorporated are neutral or slightly acid.

The stability of the compounds of this invention is also unexpected, because the inorganic polythionates, including the alkali metal salts thereof, are unstable and tend to deposit sulfur in neutral or slightly acid media and at times even in strongly acid media. Thus, aqueous solutions of potassium pentathionate and potassium hexathionate, even in a half normal hydrochloric acid solution, show signs of precipitation of sulfur after a few minutes at temperatures of 25° C. This precipitation of sulfur takes place simultaneously with the formation of lower polythionic acids. The compounds of this invention, on the other hand, in the absence of water, remain stable indefinitely. An aqueous suspension of the compounds of this invention at a pH of 1 remain stable for long periods of time, and this is particularly true of the quaternary ammonium trithionate, tetrathionate, pentathionate, and hexathionate. Their stability has been found sufficient, without the addition of any stabilizers, to allow the production of alcoholic solutions or aqueous suspensions for technical, cosmetic and therapeutic uses. Evidently, the quaternary ammonium cation has a stabilizing effect on the polythionate molecule.

The polythionates of this invention are unstable in the presence of alkali. When treated with alkaline solutions they rapidly decompose to form the corresponding thiosulfates.

The polythionates of this invention are soluble in alcohols, e.g., ethyl alcohol, isopropyl alcohol, etc., and in many organic solvents, particularly the chlorinated hydrocarbons, such as dichloroethylene.

The properties of the compounds of this invention vary with the size of the polythionate molecule and with the molecular weight of the cation. Thus, the bis-(dodecyl acetamido dimethyl benzyl) polythionate is soluble in waxes, such as those used for lipstick manufacture, and hence can be efficiently introduced into lipsticks. Most of the quaternary ammonium polythionates, however, are substantially insoluble in hydrocarbons. They have a high phenol co-efficient, i.e., germicidal efficiency. However, the larger the sulfur containing anion in general, the smaller the phenol co-efficient.

The compounds of this invention are prepared by reacting an alkali metal polythionate, preferably the potassium polythionate in aqueous solution, with an aqueous solution of the quaternary ammonium base. The reaction readily takes place as long as at least ½ mol of polythionate is present per mol of quaternary ammonium base, and the medium in which the reaction occurs has a low concentration or contains no chlorine (Cl) or sulfate ($So_4$) ions.

The reaction may be carried out at any temperature below the decomposition temperature of the reactants or of the reaction product. It proceeds readily at room temperatures (20°–25° C.), and, hence, it is preferable to operate at room temperatures. Desirably, the reaction is carried out in the presence of a solvent for the quaternary *alkyl* ammonium polythionate product. A preferred solvent is dichloroethylene.

The following examples are given for purposes of illustrating the invention. It will be understood that the invention is not limited to these examples.

GROUP I—EXAMPLES IN WHICH $R_1$ AND $R_4$ OF THE FORMULA 1 ABOVE ARE A HYDROCARBON AND AN ALKYL GROUP, RESPECTIVELY

Example 1

A solution of 50 grams of potassium tetrathionate in 1,000 cc. of water is acidified to a pH of 1 with hydrochloric acid. To this solution is added 100 cc. of a 50% solution of lauryl trimethyl ammonium chloride in isopropyl alcohol and 100 cc. of dichloroethylene while stirring. When the reaction is complete, e.g., after about 10 minutes, the dichloroethylene layer is separated from the aqueous phase and washed with water. Thereafter, the dichloroethylene solvent is evaporated by blowing air over the surface of the solution. The residual waxy solid is dried by exposure to the atmosphere at room temperature.

Upon analysis of this waxy solid by titration (after decomposition with potassium cyanide and sulfite) it shows a content of 90% bis-(lauryl trimethyl ammonium) tetrathionate; the remaining 10% is water. If dried out further the product becomes crystalline.

By the substitution of potassium pentathionate and hexathionate, respectively, for the potassium tetrathionate of this example bis-(lauryl trimethyl ammonium) pentathionate and hexathionate result.

Example 2

This example differs from Example 1 in the substitution of potassium trithionate and octadecyl trimethyl ammonium chloride for the potassium tetrathionate and lauryl trimethyl ammonium chloride, respectively, of Example 1. Bis-(octadecyl trimethyl ammonium) trithionate results. This product is a semi-crystalline solid.

Example 3

In this example, octadecyl trimethyl ammonium chloride is substituted for the lauryl trimethyl ammonium chloride of Example 1. Otherwise, the procedure is the same. Bis-(octadecyl trimethyl-ammonium) tetrathionate results. This compound is a semi-crystalline solid.

Example 4

This example differs from Example 1 in the substitution for the potassium tetrathionate of a solution containing a mixture of equal parts of penta- and hexathionate. A substantially pure bis-(lauryl trimethyl ammonia) hexathionate is first obtained as a precipitate. After most of the hexathionate has been precipitated from the solution, a precipitate of the bis-(lauryl trimethyl ammonium) penathionate is obtained. In this manner fractionation of the mixture of hexa and pentathionates may be effected.

Example 5

1,000 grams of crystalline sodium thiosulfate are dissolved in 10,000 cc. of water, the resultant solution filtered and 4 kg. of crushed ice are added. 200 cc. of $S_2Cl_2$ are dissolved in 400 cc. of ethyl ether. This solution along with 250 cc. of concentrated sulfuric acid are poured into the thiosulfate solution while stirring vigorously. The solution is then agitated by blowing air therethrough for 3 days. The sedimented sulfur is filtered off. Blowing of air through the solution is continued for 14 days, and then 20 cc. of a saturated solution of cupric acetate are added. The resultant solution is concentrated by evaporation at temperatures not over 30° C. to form a viscous solution, and the precipitated sodium sulfate is removed from this solution. The solution is then diluted with water to a volume of 1,000 cc., and 10 cc. of 50% lauryl trimethyl ammonium chloride are then added together with 25 cc. of dichloroethylene. The dichloroethylene solution is then separated from the aqueous phase, and the solvent removed by evaporation. A somewhat oily and sticky product results; this product is bis-(lauryl trimethyl ammonium) polythionate containing an average of from 8 to 10 sulfur atoms per molecule of compound. This compound is soluble in alcohol and chlorinated solvents. It is readily decomposed by alkali.

By the addition of another 10 cc. of 50% lauryl trimethyl ammonium chloride and 25 cc. of dichloroethylene to the reaction product, a new compound may be obtained having a lower average sulfur content, but containing more than 6 sulfur atoms per molecule. The new product contains about 7 to 8 sulfur atoms per molecule.

Example 6

This example differs from Example 1 in the substitution of potassium pentathionate and octadecyl trimethyl ammonium chloride for the potassium tetrathionate and lauryl trimethyl ammonium chloride, respectively, of Example 1. Bis-(octadecyl trimethyl ammonium) pentathionate is obtained as a wax-like solid.

Example 7

This example differs from Example 1 in the substitution of potassium hexathionate and octadecyl trimethyl ammonium chloride for the potassium tetrathionate and lauryl trimethyl ammonium chloride, respectively, of Example 1. Bis-(octadecyl trimethyl ammonium) hexathionate is obtained.

Example 8

This example differs from Example 1 in the substitution of potassium trithionate and hexadecyl trimethyl ammonium chloride for the potassium tetrathionate and lauryl trimethyl ammonium chloride, respectively, of Example 1. Bis-(hexadecyl trimethyl ammonium) trithionate is obtained.

Example 9

This example differs from Example 1 in the substitution of hexadecyl trimethyl ammonium chloride for lauryl trimethyl ammonium chloride of Example 1. Bis-(hexadecyl trimethyl ammonium) tetrathionate is obtained.

Example 10

This example differs from Example 1 in the substitution of potassium pentathionate and hexadecyl trimethyl ammonium chloride for the potassium tetrathionate and lauryl trimethyl ammonium chloride, respectively, of Example 1. Bis-(hexadecyl trimethyl ammonium) pentathionate is obtained.

Example 11

This example differs from Example 1 in the substitution of potassium hexathionate and hexadecyl trimethyl ammonium chloride for the potassium tetrathionate and lauryl trimethyl ammonium chloride, respectively, of Example 1. Bis-(hexadecyl trimethyl ammonium) hexathionate is obtained.

Example 12

This example differs from Example 5 in the substitution of cetyl trimethyl ammonium chloride for the lauryl trimethyl ammonium chloride of Example 5. A bis-(cetyl trimethyl ammonium) polythionate is obtained containing an average of from 8 to 10 sulfur atoms per molecule of compound.

Example 13

This example differs from the preceding example in the substitution of octadecyl trimethyl ammonium chloride for the cetyl trimethyl ammonium chloride of Example 12. Bis-(octadecyl trimethyl ammonium) polythionate having an average of from 8 to 12 sulfur atoms per molecule of compound is thus obtained.

GROUP IA—EXAMPLES IN WHICH $R_1$ AND $R_4$ OF THE FORMULA 1 ABOVE ARE ARALKYL AND ALKYL, RESPECTIVELY

Example 14

This example differs from Example 1 in the substitution of potassium trithionate and para-alkyl tolyl methyl trimethyl ammonium chloride for the potassium tetrathionate and lauryl trimethyl ammonium chloride, respectively, of Example 1. The alkyl group of the para-alkyl tolyl methyl trimethyl ammonium chloride contains from 9 to 15 carbon atoms. Bis-(para-alkyl tolyl methyl trimethyl ammonium) trithionate is obtained.

Example 15

This example differs from Example 1 in the substitution of para-alkyl tolyl methyl trimethyl ammonium chloride for the lauryl trimethyl ammonium chloride of Example 1. The alkyl group contains from 9 to 15 carbon atoms. Bis-(para-alkyl tolyl methyl trimethyl ammonium) tetrathionate is obtained.

Example 16

This example differs from Example 1 in the substitution of potassium hexathionate and para-alkyl tolyl methyl trimethyl ammonium chloride for the potassium tetrathionate and lauryl trimethyl ammonium chloride, respectively, of Example 1. Bis-(para-alkyl tolyl methyl trimethyl ammonium) hexathionate is obtained.

Example 17

This example differs from Example 5 in the substitution of para-alkyl tolyl methyl trimethyl ammonium chloride for the lauryl trimethyl ammonium chloride of Example 5. The alkyl group contains from 9 to 15 carbon atoms. Bis-(para-alkyl tolyl methyl trimethyl ammonium) polythionate is obtained having an average of from 8 to 10 sulfur atoms per molecule of compound.

GROUP II—EXAMPLES IN WHICH $R_1$ AND $R_4$ OF THE FORMULA 1 ABOVE ARE A HYDROCARBON GROUP AND AN ARALKYL GROUP, RESPECTIVELY

Example 18

This example differs from Example 1 in the substitution of potassium trithionate and lauryl dimethyl benzyl ammonium chloride for the potassium tetrathionate and lauryl trimethyl ammonium chloride, respectively, of Example 1. Bis-(lauryl dimethyl benzyl ammonium) trithionate is obtained as soft crystals.

Example 19

This example differs from Example 1 in the substitution of lauryl dimethyl benzyl ammonium chloride for the lauryl trimethyl ammonium chloride of Example 1. Bis-(lauryl dimethyl benzyl ammonium) tetrathionate is obtained.

Example 20

This example differs from Example 1 in the substitution of potassium pentathionate and lauryl dimethyl benzyl ammonium chloride for the potassium tetrathionate and lauryl trimethyl ammonium chloride, respectively, of Example 1. Bis-(lauryl dimethyl benzyl ammonium) pentathionate is obtained.

Example 21

This example differs from Example 1 in the substitution of potassium hexathionate and lauryl dimethyl benzyl ammonium chloride for the potassium tetrathionate and lauryl trimethyl ammonium chloride, respectively, of Example 1. Bis-(lauryl dimethyl benzyl ammonium) hexathionate is obtained.

Example 22

This example differs from Example 1 in the substitution of potassium trithionate and cetyl dimethyl benzyl ammonium chloride for the potassium tetrathionate and lauryl trimethyl ammonium chloride, respectively, of Example 1. Bis-(cetyl dimethyl benzyl ammonium) trithionate is obtained.

Example 23

This example differs from Example 1 in the substitution of cetyl dimethyl benzyl ammonium chloride for the lauryl trimethyl ammonium chloride of Example 1. Bis-(cetyl dimethyl benzyl ammonium) tetrathionate is obtained.

Example 24

This example differs from Example 1 in the substitution of potassium pentathionate and cetyl dimethyl benzyl ammonium chloride for the potassium tetrathionate and lauryl trimethyl ammonium chloride, respectively, of Example 1. Bis-(cetyl dimethyl benzyl ammonium) pentathionate is obtained.

Example 25

This example differs from Example 1 in the substitution of potassium hexathionate and cetyl dimethyl benzyl ammonium chloride for the potassium tetrathionate and lauryl trimethyl ammonium chloride, respectively, of Example 1. Bis-(cetyl dimethyl benzyl ammonium) hexathionate is obtained.

Example 26

This example differs from Example 1 in the substitution of potassium trithionate and alkyl dimethyl benzyl ammonium chloride for the potassium tetrathionate and the lauryl trimethyl ammonium chloride, respectively, of Example 1. The alkyl substituent is a technical mixture of lauryl and higher alkyls containing from 10 to 18 carbon atoms. The alkyl dimethyl benzyl ammonium chloride is available commercially under the trade name Rhodalon. A 50% solution of Rhodalon is used in this example. Bis-(alkyl dimethyl benzyl ammonium) trithionate is obtained.

Example 27

This example differs from Example 1 in the substitution of a 50% solution of Rhodalon for the lauryl trimethyl ammonium chloride of Example 1. Bis-(alkyl dimethyl benzyl ammonium) tetrathionate is obtained.

Example 28

This example differs from Example 1 in the substitution of potassium pentathionate and a 50% solution of Rhodalon for the potassium tetrathionate and lauryl trimethyl ammonium chloride, respectively, of Example 1. Bis-(alkyl dimethyl benzyl ammonium) pentathionate is obtained.

Example 29

This example differs from Example 1 in the substitution of potassium hexathionate and a 50% solution of Rhodalon for the potassium tetrathionate and lauryl trimethyl ammonium chloride, respectively, of Example 1. Bis-(alkyl dimethyl benzyl ammonium) hexathionate is obtained.

Example 30

This example differs from Example 1 in the substitution of potassium trithionate and an alkyl dimethyl benzyl ammonium chloride for the potassium tetrathionate and lauryl trimethyl ammonium chloride, respectively, of Example 1. The alkyl dimethyl benzyl ammonium chloride used in this example is the product sold commercially under the trade name Roccal or "BTC 50%," in which products the alkyl substituent is a mixture of alkyls having from 8 to 10 carbon atoms. Bis-(alkyl dimethyl benzyl ammonium) trithionate is obtained in which the alkyl substituent is a mixture of alkyl radicals having from 8 to 18 carbon atoms.

Example 31

This example differs from Example 1 in the substitution of Roccal for the lauryl trimethyl ammonium chloride of Example 1. Bis-(alkyl dimethyl benzyl ammonium) tetrathionate is obtained.

Example 32

This example differs from Example 1 in the substitution of potassium pentathionate and Roccal for the potassium tetrathionate and lauryl trimethyl ammonium chloride, respectively, of Example 1. Bis-(alkyl dimethyl benzyl ammonium) pentathionate is obtained.

Example 33

This example differs from Example 1 in the substitution of potassium hexathionate and Roccal for the potassium tetrathionate and lauryl trimethyl ammonium chloride, respectively, of Example 1. Bis-(alkyl dimethyl benzyl ammonium) hexathionate is obtained.

Example 34

This example differs from Example 5 in the substitution of lauryl dimethyl benzyl ammonium chloride for the lauryl trimethyl ammonium chloride of Example 5. Bis-(lauryl dimethyl benzyl ammonium) polythionate containing an average of from 8 to 10 sulfur atoms per molecule of compound is obtained.

Example 35

This example differs from Example 5 in the substitution of cetyl dimethyl benzyl ammonium chloride for the lauryl trimethyl ammonium chloride of Example 5. Bis-(cetyl dimethyl benzyl ammonium) polythionate containing an average of from 8 to 10 sulfur atoms per molecule of compound is obtained.

Example 36

This example differs from Example 5 in the substitution of a technical alkyl dimethyl benzyl ammonium chloride for the lauryl trimethyl ammonium chloride of Example 5. The technical alkyl compound employed contained a mixture of alkyl substituents having from 10 to 18 carbon atoms. Bis-(alkyl dimethyl benzyl ammonium) polythionate containing an average of from 8 to 10 sulfur atoms per molecule of compound and in which the alkyl group has from 10 to 18 carbon atoms is obtained.

Example 37

This example differs from Example 1 in the substitution of lauryl dimethyl ($\gamma$ phenyl) propyl ammonium chloride for the lauryl trimethyl ammonium chloride of Example 1. Bis-(lauryl dimethyl ($\gamma$ phenyl) propyl ammonium) tetrathionate results.

Example 38

This example differs from Example 1 in the substitution of cetyl dimethyl ($\beta$ phenyl) ethyl ammonium chloride for the lauryl trimethyl ammonium chloride of Example 1. Bis-(cetyl dimethyl ($\beta$ phenyl) ethyl ammonium) tetrathionate results.

GROUP III—EXAMPLES IN WHICH $R_1$ AND $R_4$ OF THE FORMULA 1 ABOVE ARE AN ETHER AND ARALKYL, RESPECTIVELY

Example 39

This example differs from Example 1 in the substitution of potassium trithionate and para-diisobutyl phenoxy ethoxy ethyl dimethyl benzyl ammonium chloride for the potassium tetrathionate and lauryl trimethyl ammonium chloride, respectively, of Example 1. Bis-(para-diisobutyl phenoxy ethoxy ethyl dimethyl benzyl ammonium) trithionate is obtained.

Example 40

This example differs from Example 1 in the substitution of para-diisobutyl phenoxy ethoxy ethyl dimethyl benzyl ammonium chloride for the lauryl trimethyl ammonium chloride of Example 1. Bis-(para-diisobutyl phenoxy ethoxy ethyl dimethyl benzyl ammonium) tetrathionate is obtained.

Example 41

This example differs from Example 1 in the substitution of potassium pentathionate and para-diisobutyl phenoxy ethoxy ethyl dimethyl benzyl ammonium chloride for the potassium tetrathionate and lauryl trimethyl ammonium chloride, respectively, of Example 1. Bis-(para-diisobutyl phenoxy ethoxy ethyl dimethyl benzyl ammonium) pentathionate is obtained.

Example 42

This example differs from Example 1 in the substitution of potassium hexathionate and para-diisobutyl phenoxy ethoxy ethyl dimethyl benzyl ammonium chloride for the potassium tetrathionate and lauryl trimethyl ammonium chloride, respectively, of Example 1. Bis-(para-diisobutyl phenoxy ethoxy ethyl dimethyl benzyl ammonium) hexathionate is obtained.

Example 43

This example differs from Example 1 in the substitution of potassium trithionate and para-diisobutyl cresoxy ethoxy ethyl dimethyl benzyl ammonium chloride for the potassium tetrathionate and lauryl trimethyl ammonium chloride, respectively, of Example 1. Bis-(para-diisobutyl cresoxy ethoxy ethyl dimethyl benzyl ammonium) trithionate is obtained.

Example 44

This example differs from Example 1 in the substitution of para-diisobutyl cresoxy ethoxy ethyl dimethyl benzyl ammonium chloride for the lauryl trimethyl ammonium chloride of Example 1. Bis-(para-diisobutyl cresoxy ethoxy ethyl dimethyl benzyl ammonium) tetrathionate is obtained.

Example 45

This example differs from Example 1 in the substitution of potassium pentathionate and para-diisobutyl cresoxy ethoxy ethyl dimethyl benzyl ammonium chloride for the potassium tetrathionate and lauryl trimethyl ammonium chloride, respectively, of Example 1. Bis-(para-diisobutyl cresoxy ethoxy ethyl dimethyl benzyl ammonium) pentathionate is obtained.

Example 46

This example differs from Example 1 in the substitution of potassium hexathionate and para-diisobutyl cresoxy ethoxy ethyl dimethyl benzyl ammonium chloride for the potassium tetrathionate and lauryl trimethyl ammonium chloride, respectively, of Example 1. Bis-(para-diisobutyl cresoxy ethoxy ethyl dimethyl benzyl ammonium) hexathionate is obtained.

Example 47

This example differs from Example 5 in the substitution of para-diisobutyl phenoxy ethoxy ethyl dimethyl benzyl ammonium chloride for the lauryl trimethyl ammonium chloride of Example 5. Bis-(para-diisobutyl phenoxy ethoxy dimethyl benzyl ammonium) polythionate containing an average of from 8 to 10 sulfur atoms per molecule of compound is obtained.

Example 48

This example differs from Example 5 in the substitution of para-diisobutyl toloxy ethoxy ethyl dimethyl benzyl ammonium chloride for the lauryl trimethyl ammonium chloride of Example 5. Bis-(para-diisobutyl toloxy ethoxy dimethyl benzyl ammonium) polythionate containing an average of from 8 to 10 sulfur atoms per molecule of compound is obtained.

GROUP IV—EXAMPLES IN WHICH $R_1$ AND $R_4$ OF FORMULA 1 ABOVE ARE AN AMIDE AND AN ARALKYL GROUP, RESPECTIVELY

Example 49

This example differs from Example 1 in the substitution of potassium trithionate and dodecyl acetamido dimethyl benzyl ammonium chloride for the potassium tetrathionate and lauryl trimethyl ammonium chloride, respectively, of Example 1. Bis-(dodecyl acetamido dimethyl benzyl ammonium) trithionate is obtained.

Example 50

This example differs from Example 1 in the substitution of dodecyl acetamido dimethyl benzyl ammonium chloride for the lauryl trimethyl ammonium chloride of Example 1. Bis-(dodecyl acetamido dimethyl benzyl ammonium) tetrathionate is obtained.

Example 51

This example differs from Example 1 in the substitution of potassium pentathionate and dodecyl acetamido dimethyl benzyl ammonium chloride for the potassium tetrathionate and lauryl trimethyl ammonium chloride, respectively, of Example 1. Bis-(dodecyl acetamido dimethyl benzyl ammonium) pentathionate is obtained.

Example 52

This example differs from Example 1 in the substitution of potassium hexathionate and dodecyl acetamido dimethyl benzyl ammonium chloride for the potassium tetrathionate and lauryl trimethyl ammonium chloride, respectively, of Example 1. Bis-(dodecyl acetamido dimethyl benzyl ammonium) hexathionate is obtained.

Example 53

This example differs from Example 5 in the substitution of dodecyl acetamido dimethyl benzyl ammonium chloride for the lauryl trimethyl ammonium chloride of Example 5. Bis-(dodecyl acetamido dimethyl benzyl ammonium) polythionate containing an average of from 8 to 10 sulfur atoms per molecule of compound is obtained.

GROUP V—EXAMPLES IN WHICH $R_2$, $R_3$ AND $R_4$ OF THE FORMULA 1 ABOVE ARE COMBINED WITH THE BASIC NITROGEN ATOM TO FORM A PYRIDINIUM COMPOUND

Example 54

This example differs from Example 1 in the substitution of potassium trithionate and N-lauryl pyridinium chloride for the potassium tetrathionate and lauryl trimethyl ammonium chloride, respectively, of Example 1. Bis-(N-lauryl pyridinium) trithionate is obtained as a crystalline compound.

Example 55

This example differs from Example 1 in the substitution of N-lauryl pyridinium chloride for the lauryl trimethyl ammonium chloride of Example 1. Bis-(N-lauryl pyridinium) tetrathionate is obtained.

Example 56

This example differs from Example 1 in the substitution of potassium pentathionate and N-lauryl pyridinium chloride for the potassium tetrathionate and lauryl trimethyl ammonium chloride, respectively, of Example 1. Bis-(N-lauryl pyridinium) pentathionate is obtained.

Example 57

This example differs from Example 1 in the substitution of potassium hexathionate and N-lauryl pyridinium chloride for the potassium tetrathionate and lauryl trimethyl ammonium chloride, respectively, of Example 1. Bis-(N-lauryl pyridinium) hexathionate is obtained.

Example 58

This example differs from Example 1 in the substitution of potassium trithionate and N-cetyl pyridinium chloride for the potassium tetrathionate and lauryl trimethyl ammonium chloride, respectively, of Example 1. Bis-(N-cetyl pyridinium) trithionate is obtained.

Example 59

This example differs from Example 1 in the substitution of N-cetyl pyridinium chloride for the lauryl trimethyl ammonium chloride of Example 1. Bis-(N-cetyl pyridinium) tetrathionate is obtained.

Example 60

This example differs from Example 1 in the substitution of potassium pentathionate and N-cetyl pyridinium chloride for the potassium tetrathionate and lauryl dimethyl ammonium chloride, respectively, of Example 1. Bis-(N-cetyl pyridinium) pentathionate is obtained.

Example 61

This example differs from Example 1 in the substitution of potassium hexathionate and N-cetyl pyridinium chloride for the potassium tetrathionate and lauryl trimethyl ammonium chloride, respectively, of Example 1. Bis-(N-cetyl pyridinium) hexathionate is obtained.

Example 62

This example differs from Example 5 in the substitution of lauryl pyridinium chloride for the lauryl trimethyl ammonium chloride of Example 5. Bis-(lauryl pyridinium) polythionate containing an average of from 8 to 10 sulfur atoms per molecule of compound is obtained.

Example 63

This example differs from Example 5 in the substitution of cetyl pyridinium chloride for the lauryl trimethyl ammonium chloride of Example 5. Bis-(cetyl pyridinium) polythionate containing an average of from 8 to 10 sulfur atoms per molecule of compound is obtained.

Example 64

This example differs from Example 5 in the substitution of octadecyl pyridinium chloride for the lauryl trimethyl ammonium chloride of Example 5. Bis-(octadecyl pyridinium) polythionate containing an average of from 8 to 10 sulfur atoms per molecule of compound is obtained.

GROUP VI—EXAMPLES IN WHICH $R_1$ OF THE FORMULA 1 ABOVE IS AN ESTER AND $R_2$, $R_3$ AND $R_4$ OF THIS FORMULA ARE COMBINED TO FORM A PYRIDINIUM COMPOUND

Example 65

This example differs from Example 1 in the substitution of potassium trithionate and N-(lauroyl colamino formyl methyl) pyridinium chloride for the potassium tetrathionate and lauryl trimethyl ammonium chloride, respectively, of Example 1. Bis-(N-(lauroyl colamino formyl methyl) pyridinium) trithionate is obtained. Substitution of potassium tetrathionate, pentathionate and hexathionate, respectively, for the potassium trithionate of this example results in corresponding tetrathionates, pentathionates and hexathionates, respectively.

Example 66

The example differs from Example 5 in the substitution of N-(lauroyl colamino formyl methyl) pyridinium chloride for the lauryl trimethyl ammonium chloride of Example 5. Bis-(N-(lauroyl colamino formyl methyl) pyridinium) polythionate containing an average of from 8 to 10 sulfur atoms per molecule of compound results.

GROUP VII—EXAMPLES IN WHICH $R_2$ AND $R_3$ OF THE FORMULA 1 ABOVE ARE COMBINED TO FORM A MORPHOLINIUM COMPOUND

Example 67

This example differs from Example 1 in the substitution of potassium trithionate and N-lauryl N-methyl morpholinium chloride for the potassium tetrathionate and lauryl thrimethyl ammonium chloride, respectively, of Example 1. Bis-(N-lauryl N-methyl morpholinium) trithionate is obtained.

Example 68

This example differs from Example 1 in the substitution of N-lauryl N-methyl morpholinium chloride for the lauryl trimethyl ammonium chloride of Example 1. Bis-(N-lauryl N-methyl morpholinium) tetrathionate is obtained. By the substitution of the pentathionate and hexathionate, respectively, for the tetrathionate, bis-(N-lauryl N-methyl morpholinium) penta and hexathionates are produced.

Example 69

This example differs from Example 1 in the substitution of potassium trithionate and N-cetyl N-methyl morpholinium chloride for the potassium tetrathionate and lauryl trimethyl ammonium chloride, respectively, of Example 1. Bis-(N-cetyl N-methyl morpholinium) trithionate is obtained. By the substitution of tetrathionate, pentathionate and hexathionate, respectively, for the trithionate in this example corresponding bis-(N-cetyl N-methyl morpholinium) tetrathionate, pentathionate and hexathionate are produced.

Example 70

This example differs from Example 1 in the substitution of potassium trithionate and N-alkyl N-ethyl morpholinium chloride for the potassium tetrathionate and lauryl trimethyl ammonium chloride, respectively, of Example 1. The alkyl substituent in this example contains 18 carbon atoms. Bis-(N-alkyl N-ethyl morpholinium) trithionate is obtained. By the substitution of the potassium tetrathionate, pentathionate or hexathionate, respectively, for the potassium trithionate of this example, corresponding morpholinium tetrathionates, pentathionates and hexathionates result.

Example 71

This example differs from Example 5 in the substitution of N-lauryl N-methyl morpholinium chloride for the lauryl trimethyl ammonium chloride of Example 5. Bis-(N-lauryl N-methyl morpholinium) polythionate containing an average of from 8 to 10 sulfur atoms per molecule of compound is obtained.

GROUP VIII—EXAMPLES IN WHICH $R_2$ AND $R_3$ OF FORMULA 1 ABOVE ARE COMBINED TO FORM A PIPERIDINIUM COMPOUND

Example 72

This example differs from Example 1 in the substitution of potassium trithionate and N-lauryl N-methyl piperidinium chloride for the potassium tetrathionate and lauryl trimethyl ammonium chloride, respectively, of Example 1. Bis-(N-lauryl N-methyl piperidinium) trithionate is obtained. By the substitution of potassium tetrathionate, pentathionate and hexathionate, respectively, for the potassium trithionate of this example corresponding tetrathionates, pentathionates and hexathionates result.

Example 73

This example differs from Example 1 in the substitution of potassium trithionate and N-cetyl N-methyl piperidinium chloride for the potassium tetrathionate and lauryl trimethyl ammonium chloride, respectively, of Example 1. Bis-(N-cetyl N-methyl piperidinium) trithionate is obtained. By the substitution of potassium tetrathionate, pentathionate and hexathionate, respectively, for the potassium trithionate of this example corresponding tetrathionates, pentathionates and hexathionates result.

Example 74

This example differs from Example 5 in the substitution of N-lauryl N-methyl piperidinium chloride for the lauryl trimethyl ammonium chloride of Example 5. Bis-(N-lauryl N-methyl piperidinium) polythionate containing an average of from 8 to 10 sulfur atoms per molecule of compound is obtained.

GROUP IX—EXAMPLES IN WHICH $R_2$, $R_3$ AND $R_4$ OF FORMULA 1 ABOVE ARE COMBINED TO FORM A QUINOLINIUM COMPOUND

Example 75

This example differs from Example 1 in the substitution of lauryl quinolinium chloride for the lauryl trimethyl ammonium chloride of Example 1. Bis-(lauryl quinolinium) tetrathionate is obtained.

Example 76

This example differs from Example 5 in the substitution of cetyl quinolinium chloride for the lauryl trimethyl ammonium chloride of Example 5. Bis-(cetyl quinolinium) polythionate containing an average of from 8 to 10 sulfur atoms per molecule of compound is obtained.

The new compounds of this invention possess the therapeutic properties of the polythionates and the germicidal, bactericidal and tungicidal properties of the quaternary ammonium compounds forming the cation of the compound. Hence, they can be used in the manufacture of cosmetics, such as hair tonics, lipsticks, face creams, etc., and also for medicinal uses, as an adjuvant in preparations for the treatment of skin infections, e.g., dermatological preparations.

A hair tonic embodying this invention may be made by incorporating in a preparation consisting of 70% ethyl alcohol, 4% castor oil and 26% water, 3% by weight of bis-(lauryl trimethyl ammonium) hexathionate. This compound dissolved readily producing a clear stable solution which is unusually efficacious in preventing diseases of the scalp and maintaining the latter in a healthy condition.

As many changes can be made in the above compositions and many apparently widely different embodiments of this invention can be made without departing from the scope of the claims, it is intended that all matter contained in the above description shall be interpreted as illustrative and not in a limiting sense.

Having thus described my invention, what I claim as new and desire to secure by Letters Patent of the United States is:

1. A polythionate compound [substantially insoluble] *at most somewhat soluble* in water, soluble in alcohol, and stable in acid and neutral media, and being of the general formula $$Q_2S_xO_6$$

in which Q is selected from the group consisting of (1) quaternary ammonium having four alkyl groups, one of which contains from 8 to 20 carbon atoms and each of the other three of which contains from 1 to 3 carbon atoms; (2) dialkyl morpholinium and dialkyl piperidinium, wherein one of the alkyl groups contains from 8 to 20 carbon atoms and the other form 1 to 3 carbon atoms; (3) alkyl pyridinium and alkyl iso-quinolinium, wherein the alkyl contains from 8 to 20 carbon atoms; (4) trialkyl phenyl alkyl *ammonium* in which the phenyl alkyl group contains from 7 to 15 carbon atoms, one of the other alkyl groups containing from 8 to 20 carbon atoms, and the other from 1 to 3 carbon atoms; (5) alkyl phenyl, alkyl morpholinium and piperidinium in which the alkyl group contains from 8 to 20 carbon atoms and the phenyl alkyl group from7 to 15 carbon atoms, and the cation has a molecular weight of from 190 to 470 and x is selected from the group of 3 to 10 inclusive.

2. Bis-(para-alkyl tolyl methyl trimethyl ammonium) polythionate in which the polythionate anion contains from 3 to 10 sulfur atoms and in which the alkyl group contains from 9 to 15 carbon atoms.

3. A quaternary ammonium polythionate having the formula

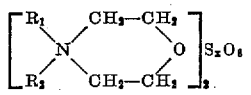

in which $R_1$ is an alkyl group containing from 8 to 20 carbon atoms, $R_2$ is an alkyl group containing from 1 to 3 carbon atoms, and x has a value of from 3 to 10 inclusive.

4. A quaternary ammonium polythionate having the formula

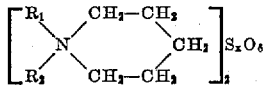

in which $R_1$ is an alkyl group containing from 8 to 20 carbon atoms, $R_2$ is an alkyl group containing from 1 to 3 carbon atoms, and x has a value of from 3 to 10 inclusive.

5. A quaternary ammonium polythionate having the formula

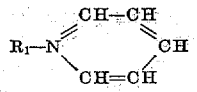

in which $R_1$ is an alkyl group containing from 8 to 20 carbon atoms, and x has a value of from 3 to 10 inclusive.

6. A quaternary ammonium polythionate having the formula

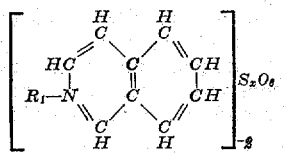

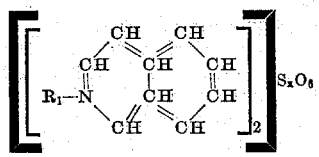

in which $R_1$ is an alkyl group containing from 8 to 20 carbon atoms, and x has a value of from 3 to 10 inclusive.

7. A process of producing a polythionate compound [substantially insoluble] *at most somewhat soluble* in water, soluble in alcohol and stable in acid and neutral media which comprises reacting an alkali metal polythionate containing from 3 to 10 atoms of sulfur with a quaternary ammonium compound having a molecular weight of from 190 to 470, and having a formula $$Q_2S_xO_6$$

in which Q is selected from the group consisting of (1) quaternary ammonium having four alkyl groups, one of which contains from 8 to 20 carbon atoms and each of the other three of which contains from 1 to 3 carbon atoms; (2) dialkyl morpholinium and dialkyl piperidinium, wherein one of the alkyl groups contains from 8 to 20 carbon atoms and the other from 1 to 3 carbon atoms; (3) alkyl pyridinium and alkyl iso-quinolinium, wherein the alkyl contains from 8 to 20 carbon atoms; (4) trialkyl phenyl alkyl *ammonium* in which the phenyl alkyl group contains from 7 to 15 carbon atoms, one of the other alkyl groups containing from 8 to 20 carbon atoms, and the other from 1 to 3 carbon atoms; (5) alkyl phenyl alkyl morpholinium and piperidinium in which the alkyl group contains from 8 to 20 carbon atoms and the phenyl alkyl group from 7 to 15 carbon atoms.

8. The process of producing a quaternary ammonium polythionate as defined in claim 7, in which the process is carried out in the presence of a solvent for the quaternary ammonium polythionate.

9. The process defined in claim 8, in which the solvent is a chlorinated hydrocarbon.

References Cited in the file of this patent or the original patent

UNITED STATES PATENTS 2,315,534 Marasco ---------- Apr. 6, 1943

OTHER REFERENCES

Kobs: "Z. Anorg. Chem.," vol. 252 (1943), pp. 119–120.

Johnson et al.: "J. Am. Chem. Soc.," vol. 73 (1951), pp. 3052–55.